United States Patent
Ghayempour et al.

(10) Patent No.: US 10,967,095 B2
(45) Date of Patent: Apr. 6, 2021

(54) WOUND DRESSINGS AND PREPARATION THEREOF

(71) Applicant: Amirkabir University of Technology, Tehran (IR)

(72) Inventors: Soraya Ghayempour, Yazd (IR); Majid Montazer, Tehran (IR); Mahnaz Mahmoudi Rad, Tehran (IR)

(73) Assignees: AMIRKABIR UNIVERSITY OF TECHNOLOGY, Tehran (IR); Soraya Ghayempour, Yazd (IR); Majid Montazer, Tehran (IR)

( * ) Notice: Subject to any disclaimer, the term of this patent is extended or adjusted under 35 U.S.C. 154(b) by 311 days.

(21) Appl. No.: 15/860,686

(22) Filed: Jan. 3, 2018

(65) Prior Publication Data

US 2018/0140738 A1    May 24, 2018

Related U.S. Application Data

(60) Provisional application No. 62/470,356, filed on Mar. 13, 2017.

(51) Int. Cl.
*A61L 15/44* (2006.01)
*A61L 15/18* (2006.01)
*A61L 15/40* (2006.01)

(52) U.S. Cl.
CPC .............. *A61L 15/44* (2013.01); *A61L 15/18* (2013.01); *A61L 15/40* (2013.01); *A61L 2300/404* (2013.01); *A61L 2300/624* (2013.01)

(58) Field of Classification Search
None
See application file for complete search history.

*Primary Examiner* — Nicole P Babson
(74) *Attorney, Agent, or Firm* — Bajwa IP Law Firm; Haris Zaheer Bajwa

(57) ABSTRACT

A method for preparing a wound dressing including forming a first solution by mixing a zinc solution with a Tragacanth solution, immersing a substrate in the first solution, forming a second solution by adjusting pH of the first solution containing the substrate, forming a modified substrate by synthesizing a plurality of ZnO nanoparticles with a particle size between 55 nm and 70 nm on the substrate by applying ultrasound radiation to the second solution, and forming a plurality of Ammoniacum nanocapsules with a particle size between 20 nm and 80 nm on the modified substrate.

13 Claims, 14 Drawing Sheets

WOUND DRESSINGS AND PREPARATION THEREOF

CROSS-REFERENCE TO RELATED APPLICATION

This application claims the benefit of priority from pending U.S. Provisional Patent Application Ser. No. 62/470,365, filed on Mar. 13, 2017, and entitled "HYDROGEL WOUND DRESSING BASED ON ENCAPSULATED NATURAL PRODUCT," which is incorporated herein by reference in its entirety.

SPONSORSHIP STATEMENT

This application has been sponsored by Iran Patent Center, which does not have any rights in this application.

TECHNICAL FIELD

The present disclosure generally relates to a method for preparing a wound dressing, particularly to a method for preparing a wound dressing including a plurality of Ammoniacum nanocapsules and a plurality of zinc oxide nanoparticles. The present disclosure further relates to a wound dressing with antibacterial and wound healing activities.

BACKGROUND

The wound is a physical injury of living tissues which is caused by a break in the epithelial integrity of the skin. The skin protects internal organs from the external environment and prevents body dehydration. Therefore, the presence of a wound may compromise the health of the patient in numerous ways. Accordingly, the healing of wounds is of great importance and using wound dressings may aid in speeding up the wound healing process.

Utilization of certain herbal products such as plant extracts and essential oils in wound dressings can lead to a rapid wound healing process with no side effect. Despite the benefits of essential oils and plant extract, their application is difficult due to their uncontrollable release.

One of the methods for incorporating essential oils and plant extract to the wound dressings is an encapsulation of the herbal products in a matrix which can control their release and increase the durability of the herbal products in the wound dressings. Natural polysaccharides such as alginate, chitin, and chitosan can speed up wound healing process and can be used as the matrix for encapsulation of herbal products. However, using herbal products individually in wound dressings may cause some side effects on the physical properties of the wound dressing substrates. The side effects may include changing the stiffness and the softness of the wound dressing substrates.

Therefore, there is a need for a wound dressing with a high antibacterial activity, high durability, no cytotoxicity, and high efficiency for wound healing. Moreover, there is a need for a simple and low-cost manufacturing process for preparation of a wound dressing with the desired characteristics.

SUMMARY

This summary is intended to provide an overview of the subject matter of the present disclosure, and is not intended to identify essential elements or key elements of the subject matter, nor is it intended to be used to determine the scope of the claimed implementations. The proper scope of the present disclosure may be ascertained from the claims set forth below in view of the detailed description below and the drawings.

In one general aspect, the present disclosure describes an exemplary method for preparing a wound dressing. The exemplary method may include forming a first solution by mixing a zinc solution with a Tragacanth solution, immersing a substrate in the first solution, forming a second solution by adjusting pH of the first solution containing the substrate, forming a modified substrate by synthesizing a plurality of ZnO nanoparticles on the substrate by applying ultrasound radiation to the second solution, and forming a plurality of Ammoniacum nanocapsules on the modified substrate.

The above general aspect may include one or more of the following features. In one exemplary embodiment, the zinc solution may have zinc (Zn) with a concentration between about 0.05 M and about 0.2 M. The Tragacanth solution may have Tragacanth with a concentration between about 0.5 and about 1.5 weight percent. In an exemplary implementation, the substrate may include a cellulosic-based substrate. In some exemplary implementations, forming the second solution by adjusting pH of the first solution containing the substrate may include adding an alkaline solution dropwise to the first solution containing the substrate to adjust pH between about 7 and about 8.

According to some exemplary implementations, forming the modified substrate by synthesizing the plurality of ZnO nanoparticles on the substrate may include applying the ultrasound radiation with a cycle between about 0.4 and about 1 and with an amplitude between about 30% and about 100% to the second solution. In some exemplary implementations, the plurality of ZnO nanoparticles may have a particle size between about 55 nm and about 70 nm.

According to some exemplary implementations, forming the plurality of Ammoniacum nanocapsules on the modified substrate may include forming a first microemulsion by adding an emulsifier to a mixture of Ammoniacum extract and oil, forming a second microemulsion by adding the Tragacanth solution to the first microemulsion, immersing the modified substrate in the second microemulsion, adding a cross-linking agent to the second microemulsion containing the modified substrate, and applying ultrasound radiation to the second microemulsion containing the modified substrate and the cross-linking agent.

According to some exemplary implementations, forming the first microemulsion may include adding a solution of the emulsifier with a concentration between 0.05 M and 0.2 M to the mixture of the Ammoniacum extract and the oil. The emulsifier may include a hydrophilic-lipophilic balance of more than about 10. In some implementations, the oil may include one of almond oil, sesame oil, coconut oil, or combinations thereof. In some implementations, the Tragacanth solution may have Tragacanth with a concentration between about 0.5 and about 1.5 weight percent.

According to some exemplary embodiments, the cross-linking agent may include aluminum chloride or calcium chloride. In some exemplary implementations, adding the cross-linking agent to the second microemulsion containing the modified substrate may include adding a solution of the cross-linking agent to the second microemulsion containing the modified substrate with a concentration between about 1.5 and about 3 weight percent.

In some exemplary implementations, applying ultrasound radiation to the second microemulsion containing the modified substrate may include applying the ultrasound radiation with a cycle between about 0.4 and about 1 and an amplitude between about 30% and about 100% for a time period between about 4 minutes and about 10 minutes. In some exemplary implementations, the plurality of Ammoniacum nanocapsules may have a particle size between about 20 nm and about 80 nm.

In another general aspect, the present disclosure describes an exemplary wound dressing. The wound dressing may include a plurality of Ammoniacum nanocapsules which may be stabilized on a modified substrate. The modified substrate may include a substrate and a plurality of ZnO nanoparticles stabilized on the substrate.

The above general aspect may include one or more of the following features. In an exemplary embodiment, each Ammoniacum nanocapsule of the plurality of Ammoniacum nanocapsules may include Ammoniacum extract encapsulated within a polymeric matrix of Tragacanth. In some exemplary implementations, each Ammoniacum nanocapsule may further include a plurality of oil particles.

According to some exemplary implementations, the plurality of ZnO nanoparticles may have a particle size between about 55 nm and about 70 nm. Each Ammoniacum nanocapsule of the plurality of Ammoniacum nanocapsules may have a particle size between about 20 nm and about 80 nm. In some implementations, the wound dressing may have a pH level between about 5.5 and about 6.5.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

In the following detailed description, numerous specific details are set forth by way of examples in order to provide a thorough understanding of the relevant teachings. However, it should be apparent that the present teachings may be practiced without such details. In other instances, well-known methods, procedures, components, and/or circuitry have been described at a relatively high-level, without detail, in order to avoid unnecessarily obscuring aspects of the present teachings.

The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown but is to be accorded the widest possible scope consistent with the principles and features disclosed herein.

Metal nanoparticles such as zinc oxide (ZnO) nanoparticles or natural products such as plant extracts are used as antibacterial active agents in conventional wound dressings. However, use of conventional wound dressings utilizing ZnO nanoparticles or natural products is rather limited due to the cytotoxicity, uncontrolled release of the active agents, inappropriate permeability to water and air, low durability, and high-cost manufacturing processes.

In order to overcome the shortcomings as described above, disclosed herein is a hydrogel-based wound dressing including Ammoniacum extract as an antibacterial wound healing agent and a plurality of ZnO nanoparticles as an antibacterial agent. The Ammoniacum extract may be encapsulated within a polymeric matrix of Tragacanth which may control the release of the Ammoniacum extract from the wound dressing to the wound site.

Figure 1A:
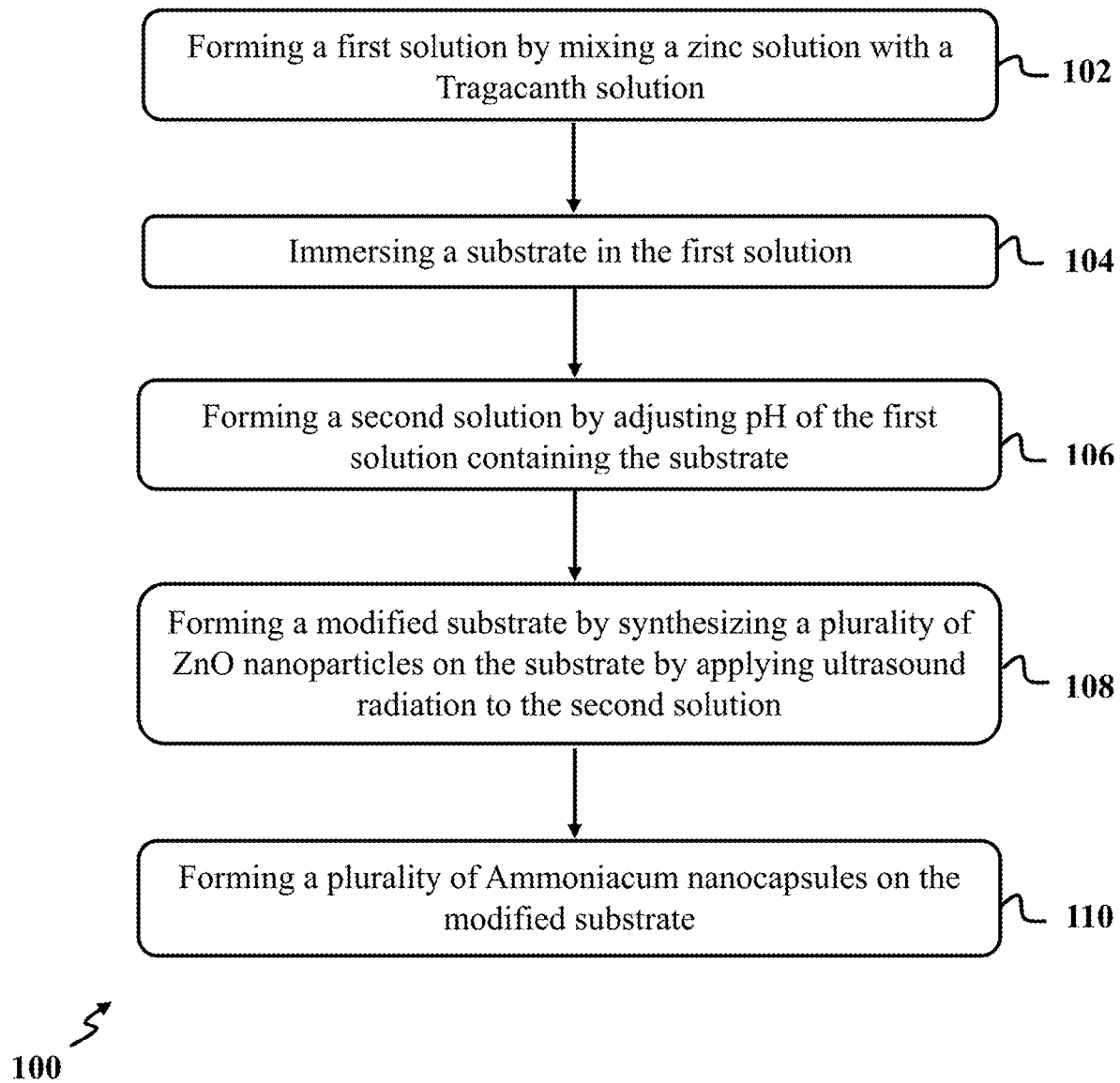
FIG. 1A illustrates a method for preparing a wound dressing, consistent with an exemplary embodiment of the present disclosure.

FIG. 1A shows an exemplary method 100 for preparing the wound dressing, consistent with an exemplary embodiment of the present disclosure. Method 100 may include forming a first solution by mixing a zinc solution with a Tragacanth solution (step 102), immersing a substrate in the first solution (step 104), forming a second solution by adjusting pH of the first solution containing the substrate (step 106), forming a modified substrate by synthesizing a plurality of ZnO nanoparticles on the substrate by applying ultrasound radiation to the second solution (step 108), and forming the plurality of Ammoniacum nanocapsules on the modified substrate (step 110).

Step 102 may include forming the first solution by mixing the zinc solution with the Tragacanth solution. In an exemplary implementation, mixing the zinc solution with the Tragacanth solution may be done using one of a magnetic stirrer, a mechanical stirrer, or an ultrasonic homogenizer. Mixing the zinc solution with the Tragacanth solution may be done for a time period between about 2 minutes and about 10 minutes at room temperature of about 20° C. to 30° C.

In some exemplary embodiments, the zinc solution may be prepared by dissolving a zinc-containing compound in water. The zinc-containing compound may include zinc nitrate or zinc acetate. In an exemplary embodiment, the zinc solution may include zinc (Zn) with a concentration between about 0.05 M and about 0.2 M. In some exemplary embodiments, the Tragacanth solution may be prepared by dissolving Tragacanth gum in water. The Tragacanth solution may include an aqueous solution of Tragacanth with a concentration between about 0.5 and about 1.5 weight percent of the solution.

Figure 2A:
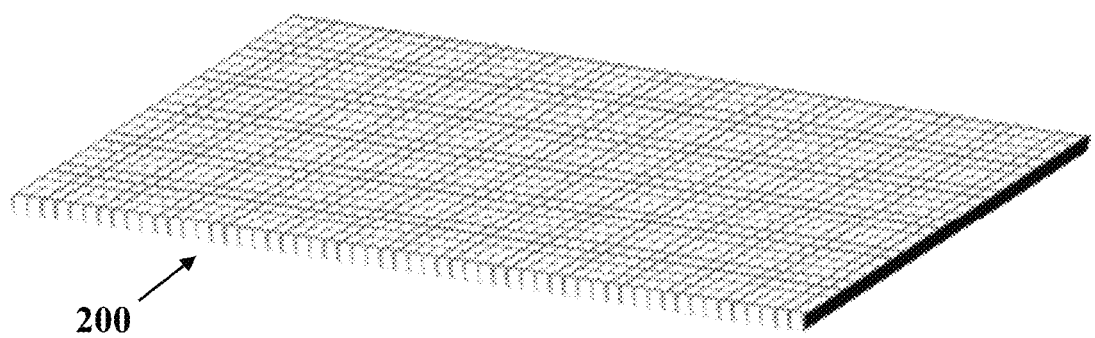
FIG. 2A illustrates a schematic view of a substrate for a wound dressing, consistent with an exemplary embodiment of the present disclosure.

Step 104 may include immersing the substrate in the first solution. In an exemplary embodiment, immersing the substrate in the first solution may include using a weight ratio of the substrate to the first solution between about 0.1 and about 0.2. FIG. 2A shows a schematic view of an exemplary substrate 200 for the wound dressing, consistent with an exemplary embodiment of the present disclosure. In some exemplary embodiments, substrate 200 may include a cellulosic-based substrate, for example, a cotton fabric.

Step 106 may include forming the second solution by adjusting pH of the first solution containing the substrate. In some implementations, adjusting pH of the first solution containing the substrate may be done by adding an alkaline solution dropwise to the first solution containing the substrate to adjust the pH between about 7 and about 8. In some exemplary embodiments, the alkaline solution may include a sodium hydroxide solution, or ammonia, or combinations thereof. In an exemplary embodiment, the alkaline solution may have a concentration between about 0.5 and about 2 M.

Step 108 may include forming the modified substrate by synthesizing the plurality of ZnO nanoparticles on the substrate by applying ultrasound radiation to the second solution. In some exemplary embodiments, the ultrasound radiation may have a cycle between about 0.4 and about 1 and amplitude between about 30% and about 100%. In some exemplary embodiments, the ultrasound radiation may be applied to the second solution for a time period between about 4 minutes and about 10 minutes.

Figure 2B:
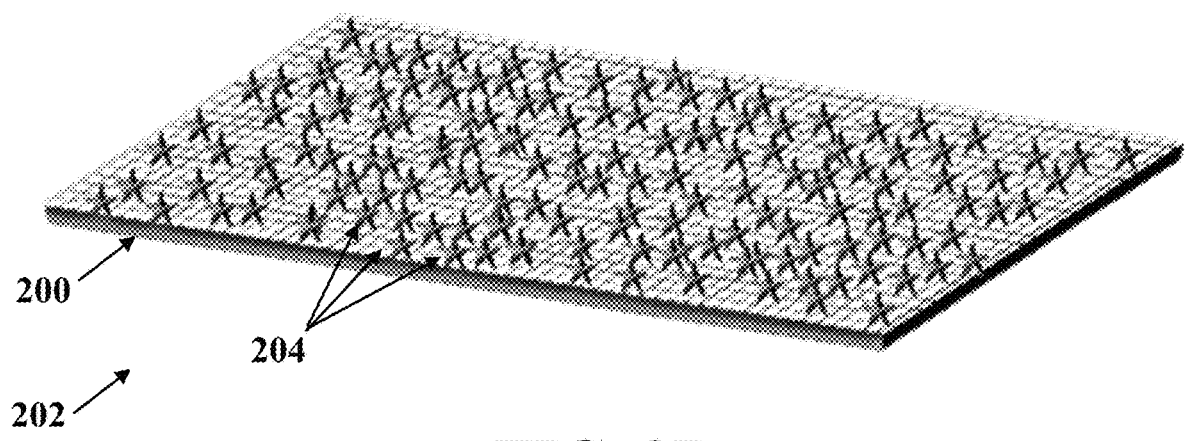
FIG. 2B illustrates a schematic view of the modified substrate, consistent with an exemplary embodiment of the present disclosure.

FIG. 2B shows a schematic view of an exemplary modified substrate 202 including the plurality of ZnO nanoparticles 204, consistent with an exemplary embodiment of the present disclosure. In some exemplary embodiments, the plurality of ZnO nanoparticles 204 may have a star-like shape with a particle size between about 55 nm and about 70 nm. In an exemplary embodiment, the plurality of ZnO nanoparticles 204 may be uniformly stabilized on the substrate 200. In some exemplary embodiments, stabilizing the plurality of ZnO nanoparticles 204 on the substrate 200 may include spreading out the plurality of ZnO nanoparticles 204 over the substrate 200 through performing chemical interactions, for example, hydrogen bonds.

In some exemplary embodiments, stabilization of the plurality of ZnO nanoparticles 204 on substrate 200 may be done through forming hydrogen bonds between hydroxyl groups of the Tragacanth and the cellulose molecules of the substrate 200. In some exemplary embodiments, the plurality of ZnO nanoparticles 204 may be further stabilized on substrate 200 due to the interactions between carboxyl groups of the Tragacanth and the cellulose molecules of substrate 200.

Figure 1B:
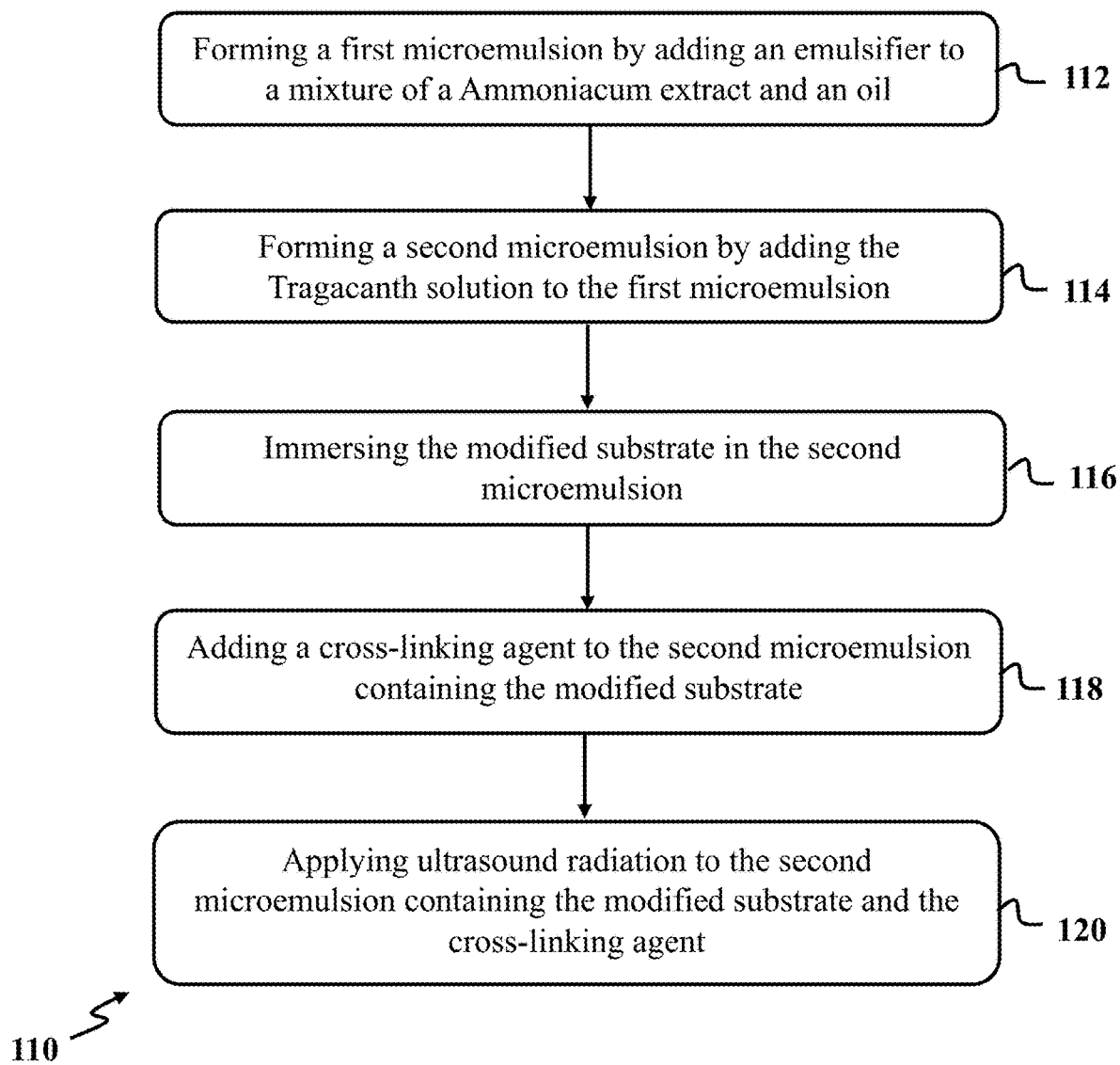
FIG. 1B illustrates a method for forming a plurality of Ammoniacum nanocapsules on the modified substrate, consistent with an exemplary embodiment of the present disclosure.

Step 110 may include forming the plurality of Ammoniacum nanocapsules on the modified substrate. FIG. 1B shows an exemplary implementation of step 110 for forming the plurality of Ammoniacum nanocapsules on the modified substrate, consistent with an exemplary embodiment of the present disclosure. Forming the plurality of Ammoniacum nanocapsules on the modified substrate may include forming a first microemulsion by adding an emulsifier to a mixture of Ammoniacum extract and oil (step 112), forming a second microemulsion by adding the Tragacanth solution to the first microemulsion (step 114), immersing the modified substrate in the second microemulsion (step 116), adding a cross-linking agent to the second microemulsion containing the modified substrate (step 118), applying ultrasound radiation to the second microemulsion containing the modified substrate and the cross-linking agent (step 120).

Step 112 may include forming the first microemulsion by adding the emulsifier to the mixture of the Ammoniacum extract and the oil. In some exemplary implementations, the mixture of the Ammoniacum extract and the oil may be prepared by mixing the Ammoniacum extract and oil using one of a magnetic stirrer, a mechanical stirrer, or an ultrasonic homogenizer. In some exemplary embodiments, mixing the Ammoniacum extract and oil may be done during a time period between about 2 minutes and about 10 minutes at room temperature. In an exemplary embodiment, the mixture of the Ammoniacum extract and the oil may include a weight ratio of the Ammoniacum extract to the oil between about 2 and about 3.

In some exemplary embodiments, the first microemulsion may include a water in oil (W/O) microemulsion including a plurality of micelles with a hydrophilic center of the Ammoniacum extract and a hydrophobic surface of oil particles. The Ammoniacum extract in the hydrophilic center may be trapped with the plurality of oil particles such as almond oil, sesame oil, coconut oil, or combinations thereof. In some exemplary embodiments, the emulsifier may include ionic emulsifiers with a hydrophilic-lipophilic balance (HLB) more than about 10 such as Triton X-100, Polysorbate 80, or Polysorbate 20. The emulsifier may be present in the first microemulsion with a concentration between about 0.05 M and about 0.2 M.

Step 114 may include forming the second microemulsion by adding the Tragacanth solution to the first microemulsion. In some exemplary implementations, the Tragacanth solution may be added to the first microemulsion dropwise while stirring the first microemulsion using one of a homogenizer, a stirrer, an agitator, or combinations thereof. In some exemplary embodiments, the Tragacanth solution may include a concentration of Tragacanth between about 0.5 and about 1.5 weight percent.

In some exemplary embodiments, the second microemulsion may include a water in oil in water (W/O/W) microemulsion. In some exemplary embodiments, adding the Tragacanth to the first microemulsion may create a new outer layer to the W/O micelles of the first microemulsion, and may convert the W/O micelles to the W/O/W micelles. In some exemplary embodiments, the Tragacanth may surround almond oil and Ammoniacum extract and may form two-layer W/O/W micelles.

Step 116 may include immersing the modified substrate in the second microemulsion. In some exemplary embodiments, immersing the modified substrate in the second microemulsion may include using a weight ratio of the modified substrate to the second microemulsion between about 0.1 and about 0.2.

Step 118 may include adding a cross-linking agent to the second microemulsion containing the modified substrate. In some exemplary implementations, adding a cross-linking agent to the second microemulsion containing the modified substrate may include adding a solution of the cross-linking agent to the second microemulsion containing the modified substrate with a concentration between about 1.5 and about 3 weight percent. In some exemplary embodiments, the cross-linking agent may include aluminum chloride or calcium chloride.

Step 120 may include applying ultrasound radiation to the second microemulsion containing the modified substrate and the cross-linking agent. In some exemplary embodiments, the ultrasound radiation may have a cycle between about 0.4 and about 1, and an amplitude between about 30% and about 100%. In some exemplary embodiments, the ultrasound radiation may be applied to the second microemulsion containing the modified substrate for a time period between about 4 minutes and about 10 minutes.

In some exemplary embodiments, using the ultrasound radiation for forming and stabilizing the plurality of Ammoniacum nanocapsules on the modified substrate may lead to reduce the time required for preparing the wound dressing and high encapsulation efficiency of the Ammoniacum extract in the polymeric matrix of Tragacanth without any side effect on the structural and physical properties of the modified substrate such as stiffness and softness.

In some implementations, forming the plurality of Ammoniacum nanocapsules on the modified substrate may include encapsulating the Ammoniacum extract in the polymeric matrix of Tragacanth to form the plurality of Ammoniacum nanocapsules, and stabilizing the plurality of Ammoniacum nanocapsules on the modified substrate with the plurality of ZnO nanoparticles. In some exemplary embodiments, the plurality of Ammoniacum nanocapsules on the modified substrate may include spreading out the plurality of Ammoniacum nanocapsules over the modified substrate through forming chemical interactions, for example, hydrogen bonds.

In an exemplary embodiment, encapsulating the Ammoniacum extract in the polymeric matrix of Tragacanth to form the plurality of Ammoniacum nanocapsules, and stabilizing the plurality of Ammoniacum nanocapsules on the modified substrate may be carried out simultaneously.

Figure 2C:
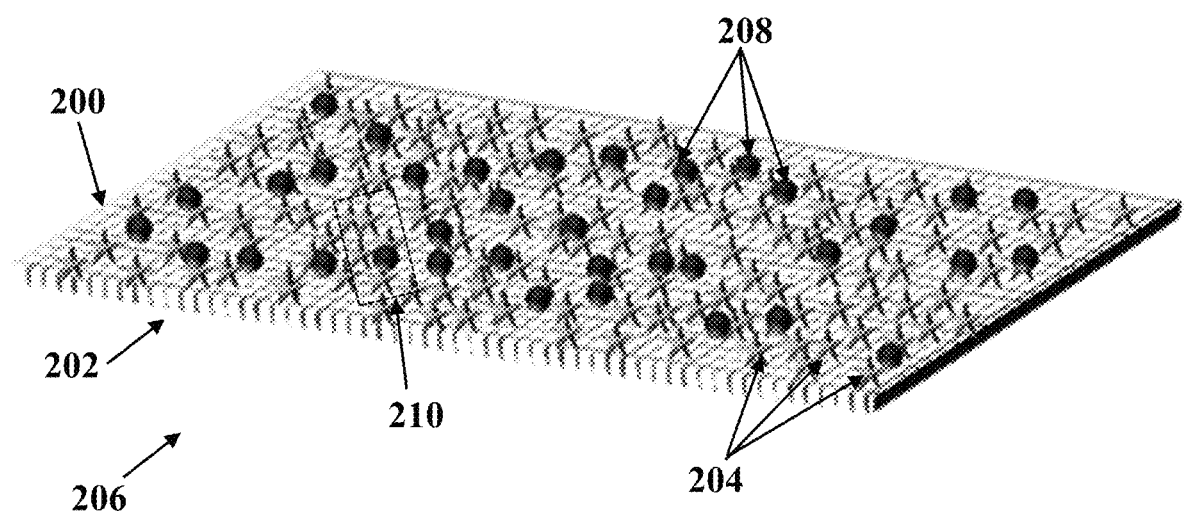
FIG. 2C illustrates a schematic view of an exemplary wound dressing, consistent with an exemplary embodiment of the present disclosure.

FIG. 2C shows a schematic view of wound dressing 206, consistent with an exemplary embodiment of the present disclosure. Referring to FIG. 2C wound dressing 206 may include the plurality of Ammoniacum nanocapsules 208 which may be formed and stabilized on modified substrate 202, which may include ZnO nanoparticles 204 on substrate 200.

Figure 2D:
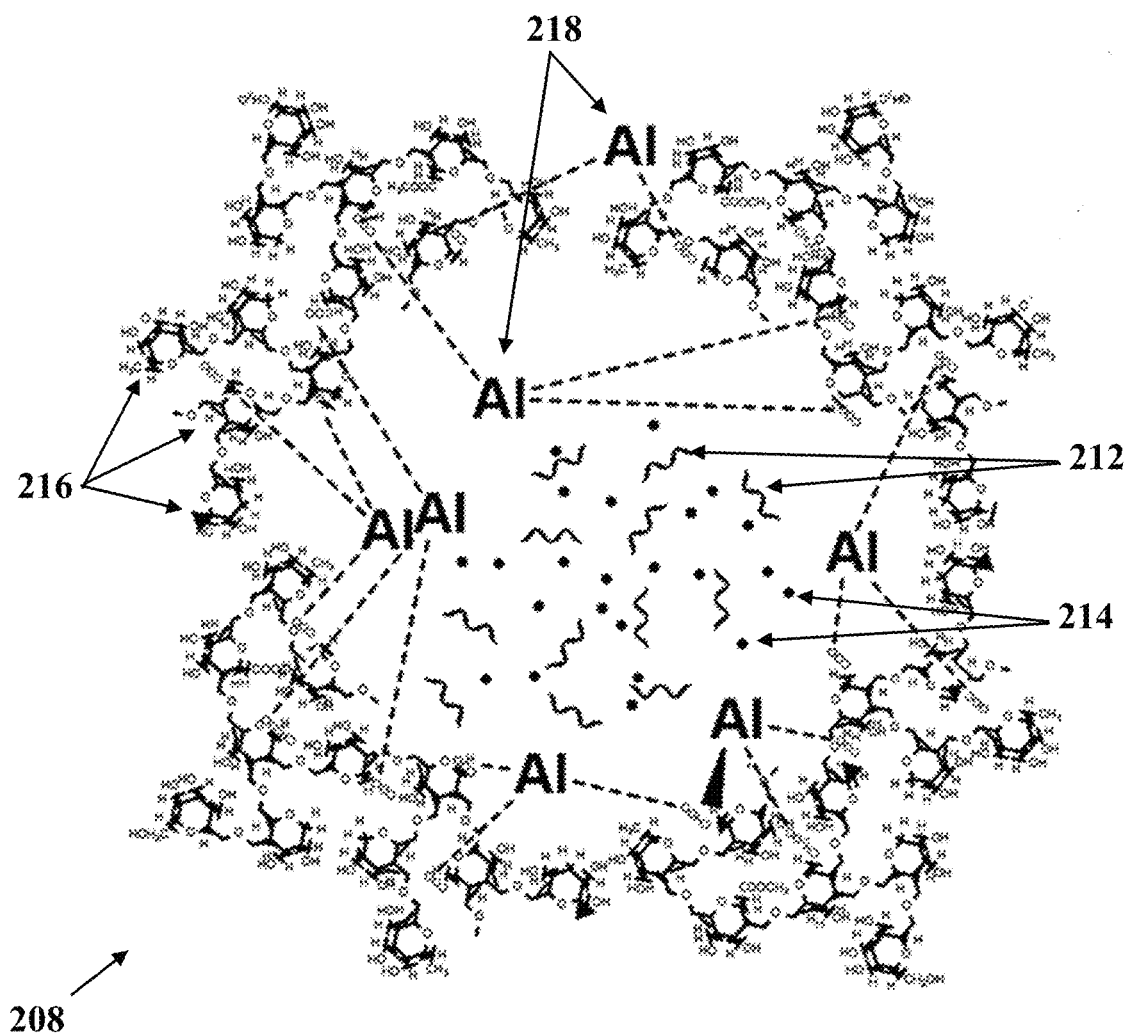
FIG. 2D illustrates a schematic view of an Ammoniacum nanocapsule, consistent with an exemplary embodiment of the present disclosure.

FIG. 2D shows a schematic view of an example of the plurality of Ammoniacum nanocapsules 208, consistent with an exemplary embodiment of the present disclosure. The exemplary Ammoniacum nanocapsules 208 may include Ammoniacum extract 212 and oil particles 214 encapsulated within the Tragacanth 216. In some exemplary embodiments, the plurality of Ammoniacum nanocapsules 208 may have a particle size between about 20 nm and about 80 nm. In some exemplary embodiments, encapsulating the Ammoniacum extract 212 and oil particles 214 in the polymeric matrix of Tragacanth 216 may be done through creating chemical interactions, for example, hydrogen bonds between aluminum (Al) ions 218 of the cross-linking agent and carboxyl groups of the Tragacanth 216.

Figure 2E:
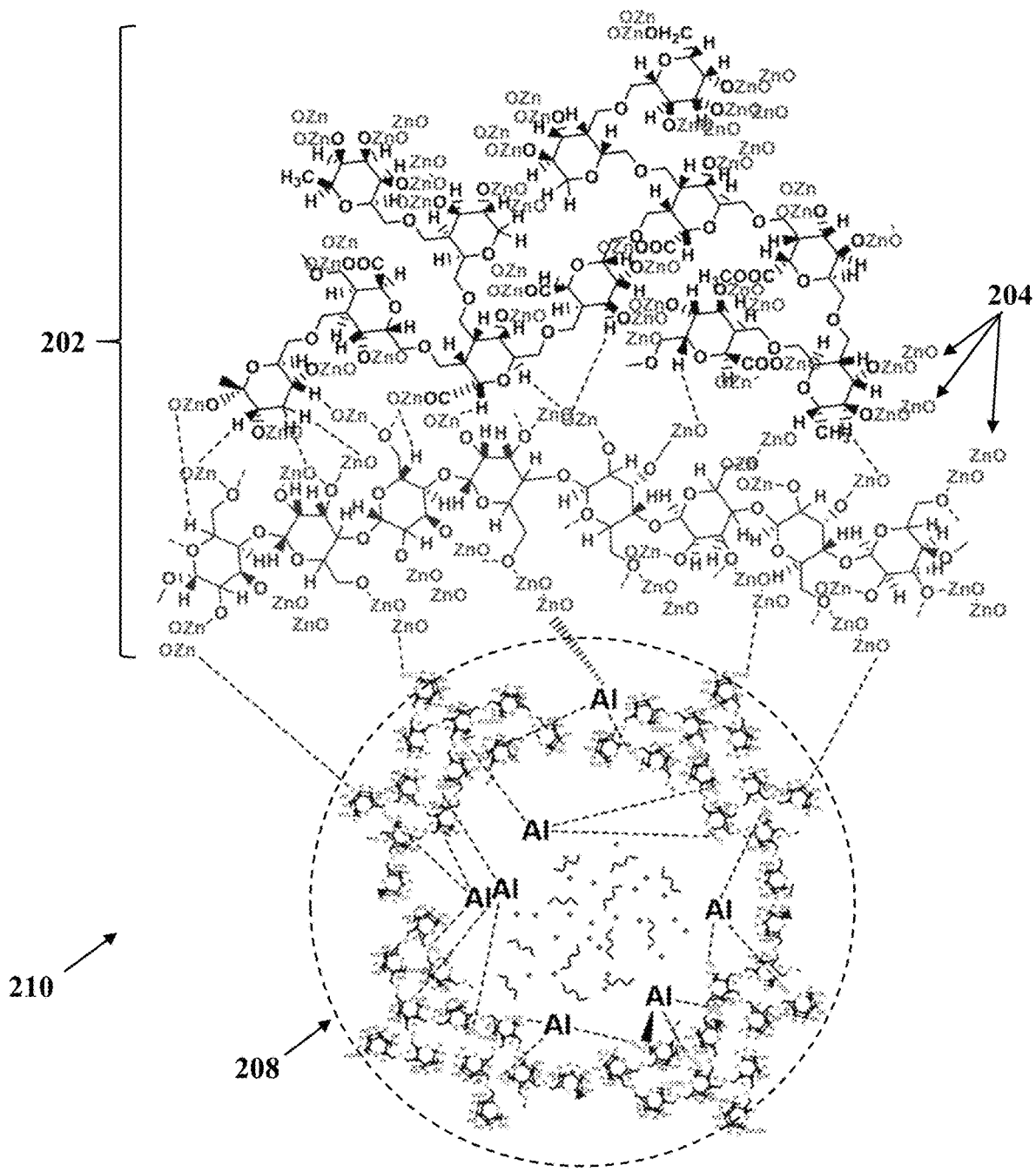
FIG. 2E illustrates a schematic view of a portion of the wound dressing, consistent with an exemplary embodiment of the present disclosure.

FIG. 2E shows a schematic view of an exemplary portion 210 of the exemplary wound dressing 206 shown in FIG. 2C, consistent with an exemplary embodiment of the present disclosure. The exemplary portion 210 shows that the Ammoniacum nanocapsule 208 may be stabilized on the modified substrate 202 including the plurality of ZnO nanoparticles 204. In some exemplary embodiments, the plurality of Ammoniacum nanocapsules 208 on the modified substrate 202 may include spreading out the plurality of Ammoniacum nanocapsules 208 over the modified substrate 202 through forming chemical interactions, for example, hydrogen bonds.

In some exemplary embodiments, stabilizing the plurality of Ammoniacum nanocapsules 208 on the modified substrate 202 may be done through forming intermolecular hydrogen bonds and interactions between aluminum ions 218 of the cross-linking agent and the plurality of ZnO nanoparticles 204 of modified substrate 202 as shown in FIG. 2D.

In some implementations, in order to prepare the wound dressing 206 for end use and wound healing applications, the wound dressing 206 may be washed and dried after forming the plurality of Ammoniacum nanocapsules on the modified substrate (step 110). In some exemplary embodiments, washing the wound dressing 206 may include rinsing the wound dressing 206 with water up to three times for removing the excess amount of material that may remain in the wound dressing 206. In an exemplary embodiment, drying the washed wound dressing 206 may be done at room temperature between about 20° C. and 30° C.

In some exemplary embodiments, the wound dressing 206 may include a hydrogel-based wound dressing due to the presence of the Tragacanth which creates a moist environment for keeping water in the wound dressing 206 for a long time, for example, about twenty-four (24) hours. In an exemplary embodiment, the wound dressing 206 may have a pH level between about 5.5 and about 6.5. In some exemplary embodiments, the wound dressing 206 may have a high permeability to water and air which may accelerate a wound healing process.

EXAMPLES

Example 1

Morphological Characterizations of the Wound Dressing

Figure 3A:
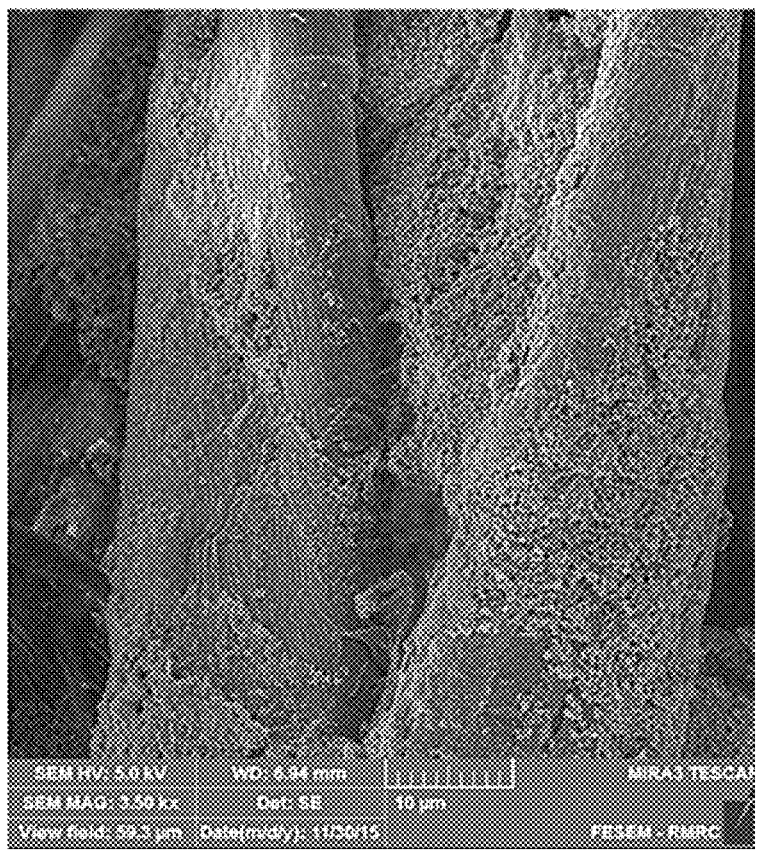
FIG. 3A illustrates a field emission scanning electron microscope (FESEM) image of an exemplary wound dressing, consistent with an exemplary embodiment of the present disclosure.
Figure 3B:
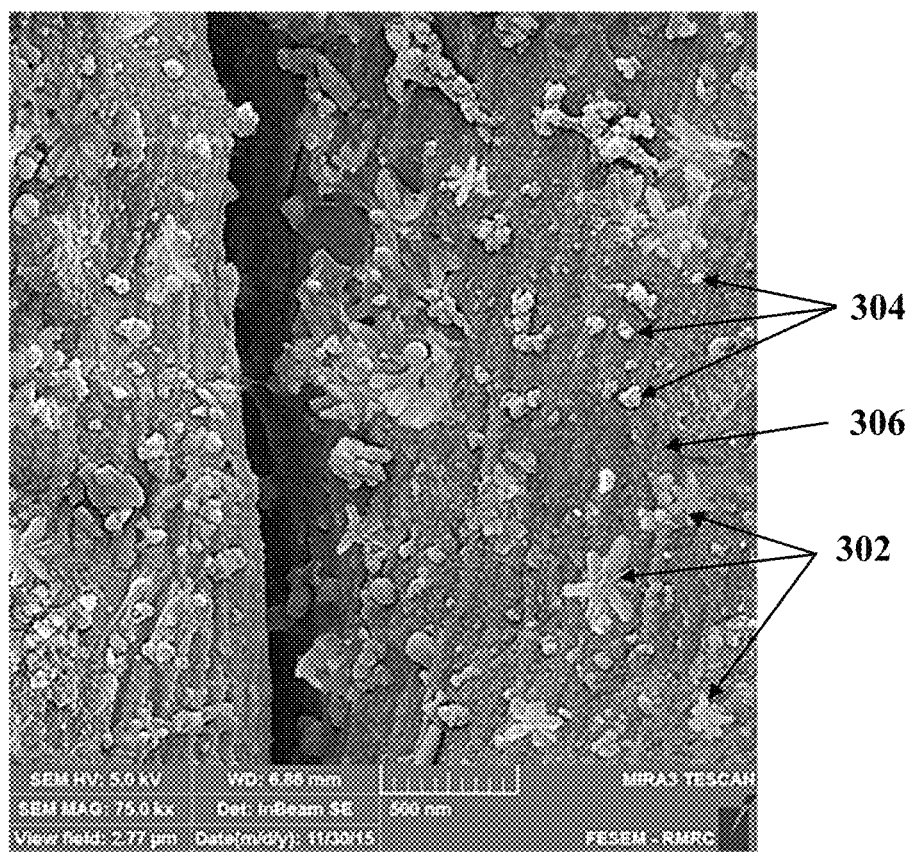
FIG. 3B illustrates a magnified FESEM image of an exemplary wound dressing, consistent with an exemplary embodiment of the present disclosure.

In this example, morphological characterizations of an exemplary wound dressing, which was prepared as described accordingly to exemplary embodiments in the present disclosure, was studied using electron microscopy. FIG. 3A shows a field emission scanning electron microscopy (FESEM) image of the wound dressing, consistent with an exemplary embodiment of the present disclosure. FIG. 3B shows a magnified FESEM image of the wound dressing, consistent with an exemplary embodiment of the present disclosure.

Referring to FIGS. 3A and 3B, the FESEM images show that exemplary ZnO nanoparticles 302 and Ammoniacum nanocapsules 304 are homogenously stabilized on the surface of the exemplary cotton fabric 306 of the wound dressing through forming hydrogen bonds between the Tragacanth molecules and the cellulose molecules of the cotton fabric 306. Moreover, it may be observed that ZnO nanoparticles 302 are star-like particles, and Ammoniacum nanocapsules 304 have spherical shapes.

Example 2

Fourier-Transform Infrared Analysis of the Wound Dressing

Figure 4:
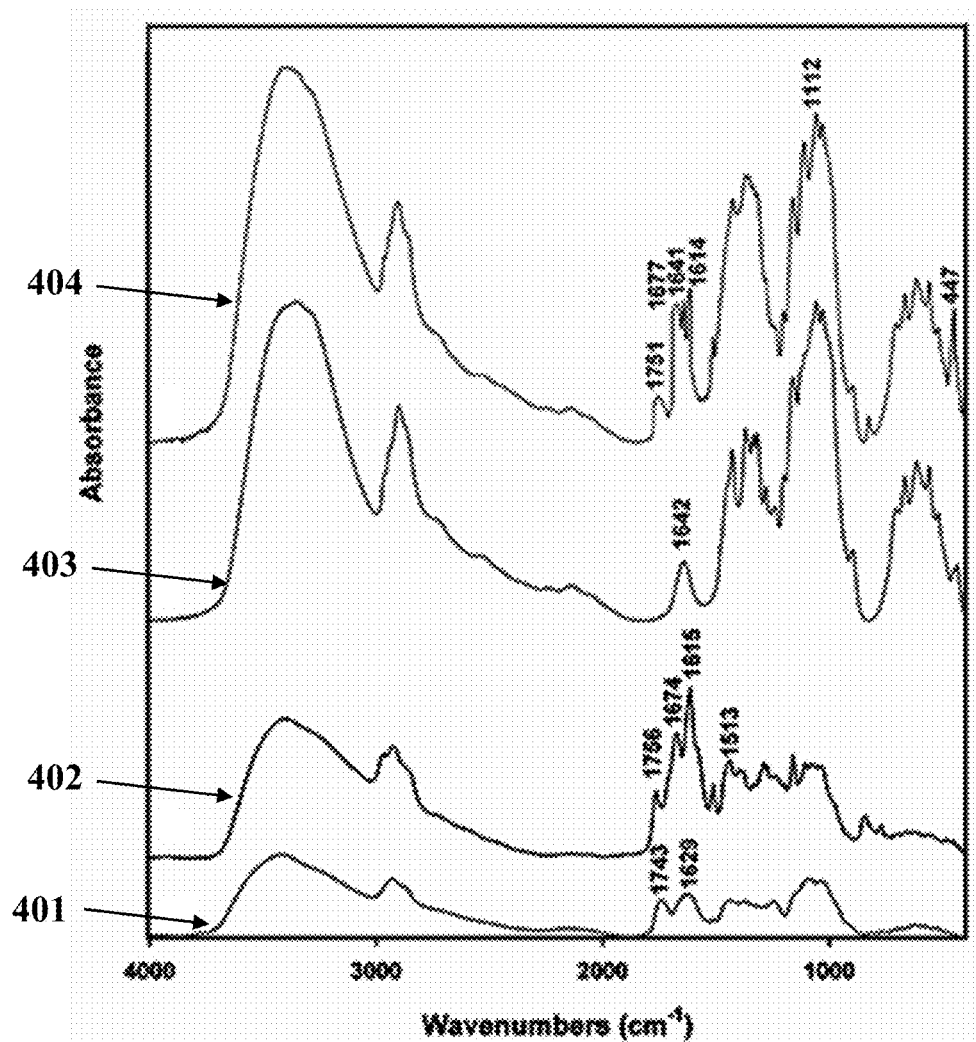
FIG. 4 illustrates Fourier-transform infrared (FT-IR) spectra of Tragacanth, Ammoniacum extract, cellulosic substrate, and an exemplary wound dressing, consistent with an exemplary embodiment of the present disclosure.

In this example, the structure of an exemplary wound dressing, which was prepared as described in exemplary embodiments of the present disclosure, was studied by comparing Fourier-transform infrared (FT-IR) spectra of the exemplary wound dressing and its components. FIG. 4 shows FT-IR spectra of Tragacanth 401, Ammoniacum extract 402, the cellulosic substrate 403, and the exemplary wound dressing 404, consistent with an exemplary embodiment of the present disclosure. The spectrum of Tragacanth 401 shows a wide peak at a wavelength about 3420 cm$^{-1}$ due to the presence of hydroxyl groups, and a peak at a wavelength about 2927 cm$^{-1}$ due to the presence of methylene groups. Moreover, two more peaks appeared in the spectrum of Tragacanth 401 at the wavelengths of about 1743 cm$^{-1}$ and about 1629 cm$^{-1}$ due to the presence of carbonyl and carboxyl groups of Tragacanth.

Referring to FIG. 4, the spectrum of Ammoniacum extract 402 includes two peaks at wavelengths of about 1515 cm$^{-1}$ and about 1615 cm$^{-1}$ for the aromatic double bond, which are appeared due to the presence of aromatic compounds such as α-Bisabolol, and aromatic compounds with carboxylic groups such as β-Cyclocitral, β-Ionone, and benzyl benzoate. Furthermore, a peak related to the carboxylate groups at a wavelength of about 1674 cm$^{-1}$ and a peak of the carbonyl groups at a wavelength of about 1756 cm$^{-1}$ appeared in the spectrum of Ammoniacum extract 402.

Referring again to FIG. 4, there are several peaks for stretching vibrations of different groups in the spectrum of the cellulosic substrate 403. For example, a peak for O—H groups at a wavelength of about 3347 cm$^{-1}$, a peak for aliphatic C—H groups at a wavelength of about 2900 cm$^{-1}$, and a peak for C—O—C groups at a wavelength of about 1058 cm$^{-1}$ may be observed.

With more reference to FIG. 4, the spectrum of the exemplary wound dressing 404 includes a peak at a wavelength about 449 cm$^{-1}$ for stretching vibrations of Zn—O bonds, which confirms the in-situ synthesis of ZnO nanoparticles on the surface of the substrate, for example, the cotton fabric. Moreover, the formation of Ammoniacum nanocapsules on the substrate is proved with the appearance of the peak related to Al—O—C bond at a wavelength about 1112 cm$^{-1}$. The Al—O—C bond is between aluminum (Al) of AlCl$_3$ cross-linking agent, oxygen (O) of the ZnO nanoparticles, and the carbon (C) of the Tragacanth which creates the outer layer of the Ammoniacum nanocapsules.

Furthermore, there are several peaks for aromatic double bonds and the carboxylate groups of the Ammoniacum extract in the spectrum of the exemplary wound dressing 404 at wavelengths of about 1614 cm$^{-1}$ and about 1677 cm$^{-1}$, which confirms the presence of the Ammoniacum extract in the nanocapsules. Also, in the spectrum of the exemplary wound dressing 404, there is a peak at a wavelength of about 1751 cm$^{-1}$ due to the combination of stretching vibrations of different groups such as carbonyl groups of Tragacanth at a wavelength of about 1743 cm$^{-1}$, and carbonyl groups in Ammoniacum extract at a wavelength of about 1756 cm$^{-1}$.

Example 3

Cytotoxicity Assay of the Wound Dressing

In this example, cytotoxicity of the exemplary wound dressing, which was prepared as described in exemplary embodiments of the present disclosure, was studied using 3-(4,5-dimethylthiazol-2-yl)-2,5 diphenyltetrazolium bromide (MTT) assay on human fibroblast cells. At first, the human fibroblast cells were exposed to the wound dressing, and after that, the MTT assay was performed to evaluate the biocompatibility and cytotoxicity of the exemplary wound dressing. In the MTT assay, the live cells have the ability to absorb and reduce the yellow Tetrasol dye to violet Formazan dye, while the dead cells can not react with the Tetrasol dye.

Figure 5:
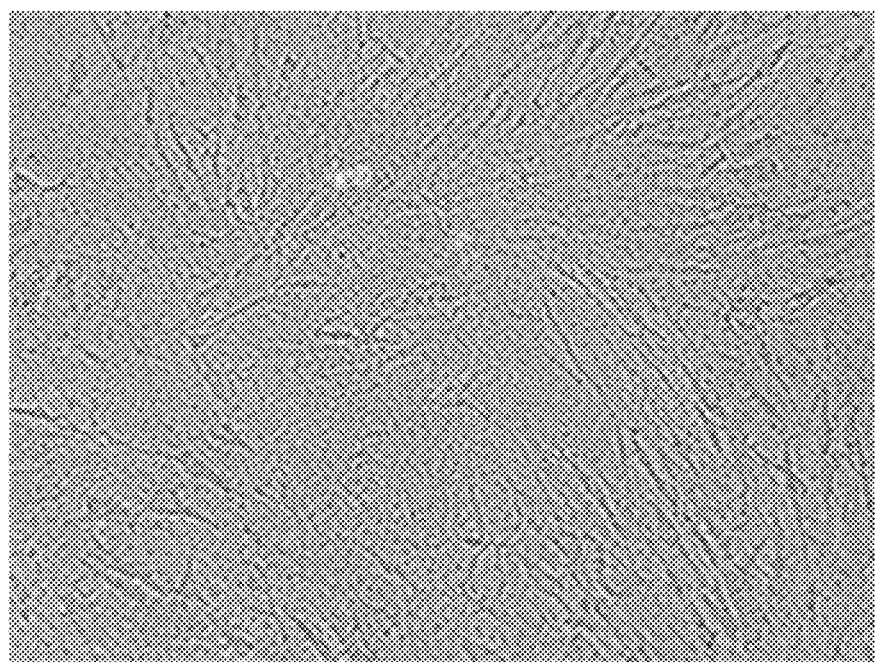
FIG. 5 illustrates cytotoxicity assay of an exemplary wound dressing, consistent with an exemplary embodiment of the present disclosure.

FIG. 5 shows human fibroblast cells after performing cytotoxicity assay of the wound dressing, consistent with an exemplary embodiment of the present disclosure. It may be seen that the fibroblast cells have an acceptable growth and proliferation in the culture medium, and they still have a spindle-shaped appearance. According to the formed violet color in the plate containing the human fibroblast cells, the majority of the cells are survived. Also, the cell viability which is a percentage of the live cells is about 93% after exposing the cells to the wound dressing. Therefore, the wound dressing shows very low cytotoxicity which can be attributed to the presence of the safe materials in the wound dressing such as Tragacanth gum as the natural polymer and Ammoniacum extract as the wound healing agent.

Example 4

Antibacterial Assay of the Wound Dressing

In this example, the antibacterial activity of the wound dressing, which was prepared as described in exemplary embodiments of the present disclosure, was studied using the colony counting method and the agar diffusion method. TABLE. 1 represents the results of the antibacterial activity of the exemplary wound dressing.

TABLE 1

Antibacterial activity assay results for the exemplary wound dressing conducted by colony counting and Agar diffusion method

| Method Parameter | Colony counting method Microbial reduction (%) | Agar diffusion method Zone of inhibition (mm) |
|---|---|---|
| *Escherichia coli* | 100 | 3.3 ± 0.1 |
| *Staphylococcus aureus* | 100 | 3.3 ± 0.1 |
| *Pseudomonas aeruginosa* | 100 | 3.4 ± 0.1 |

Referring to TABLE. 1, results of both methods indicate high antibacterial activity of the wound dressing against different bacteria such as *Escherichia coli*, *Staphylococcus aureus*, and *Pseudomonas aeruginosa*. The high antibacterial activity of the wound dressing may be attributed to the presence of ZnO nanoparticles which has a positive effect on the antimicrobial activity of the wound dressing.

Example 5

Wound Healing Assay of the Wound Dressing

In this example, wound healing activity of the wound dressing, which was prepared as described in exemplary embodiments of the present disclosure, was investigated through creating a scratch on the monolayer of human primary fibroblast cells and considering the restoration stages of the scratch.

Figure 6A:
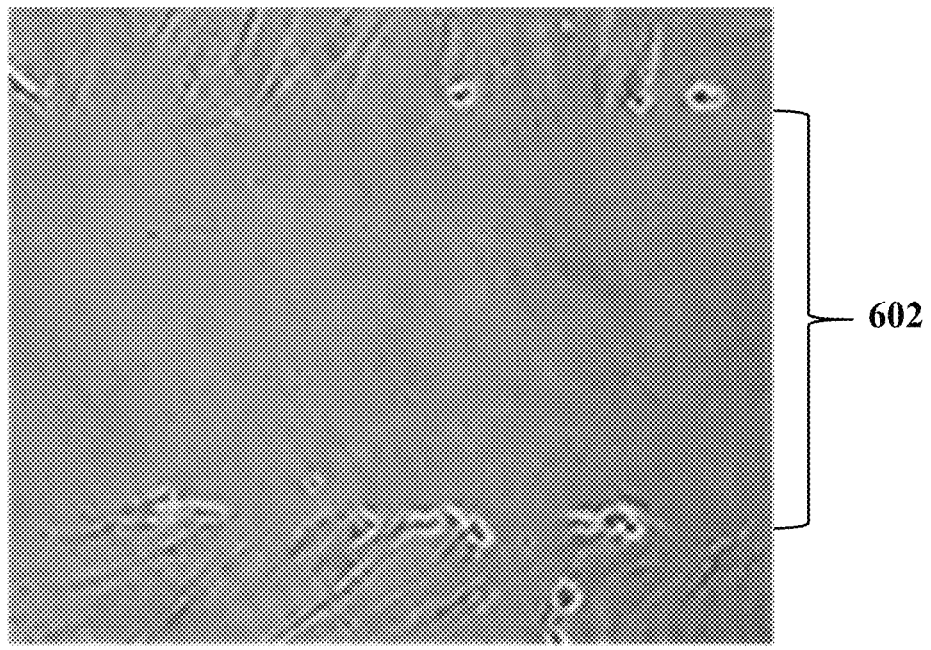
FIG. 6A illustrates a monolayer of human fibroblast cells with a scratch, consistent with an exemplary embodiment of the present disclosure.
Figure 6B:
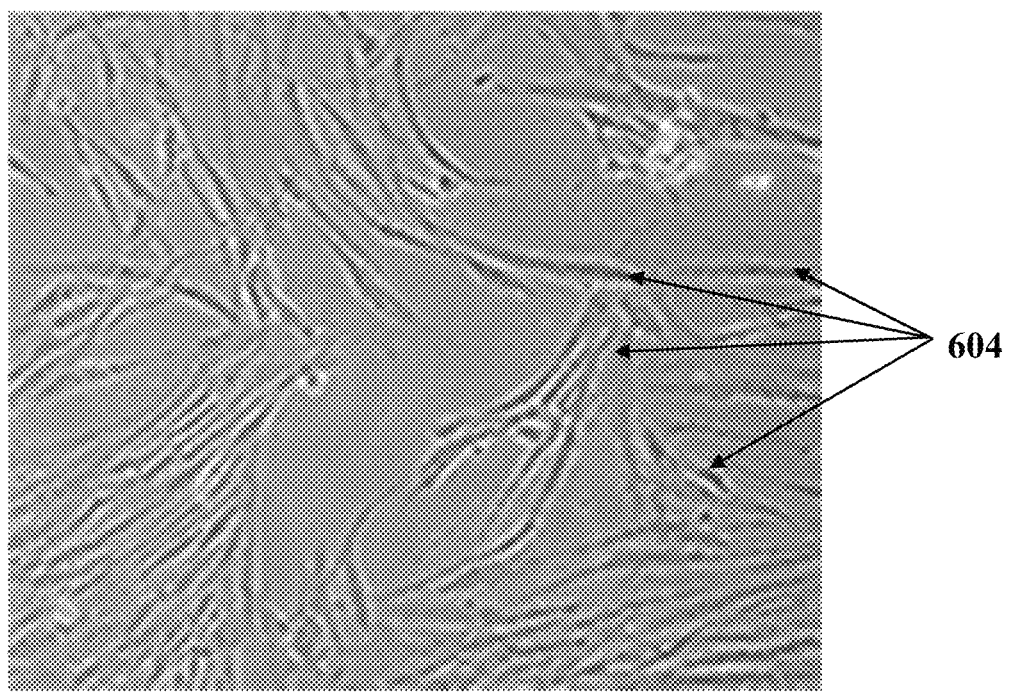
FIG. 6B illustrates the monolayer of human fibroblast cells twenty-four hours after creating the scratch, consistent with an exemplary embodiment of the present disclosure.
Figure 6C:
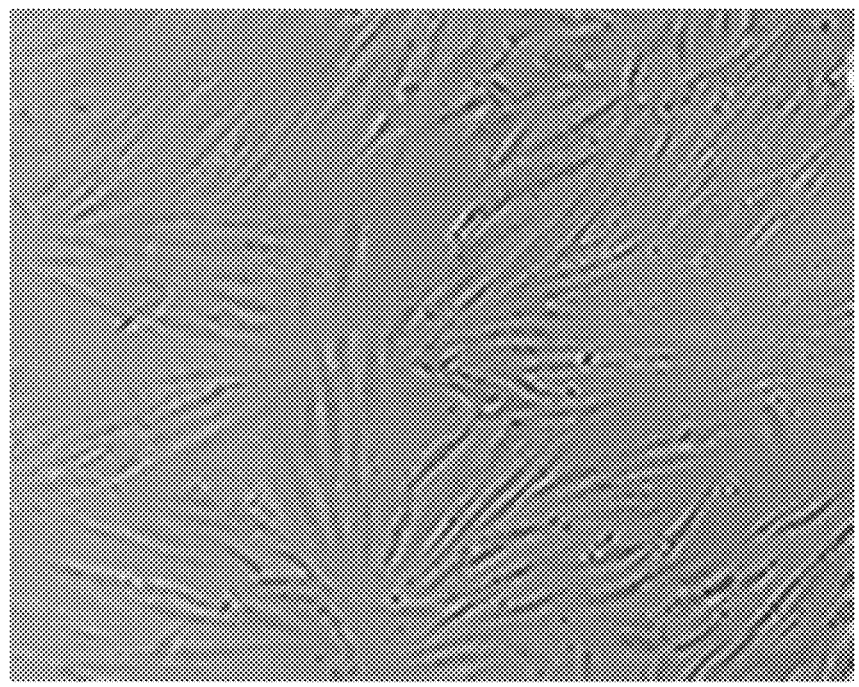
FIG. 6C illustrates the monolayer of human fibroblast cells forty-eight hours after creating the scratch, consistent with an exemplary embodiment of the present disclosure.

FIG. 6A shows the human primary fibroblast cells at the baseline of the wound healing assay of the wound dressing, consistent with an exemplary embodiment of the present disclosure. FIG. 6B shows the human primary fibroblast cells about 24 hours after performing the wound healing assay of the wound dressing, consistent with an exemplary embodiment of the present disclosure. FIG. 6C shows the human primary fibroblast cells about 48 hours after performing the wound healing assay of the wound dressing, consistent with an exemplary embodiment of the present disclosure.

Referring to FIGS. 6A and 6B, cells 604 moved from two sides of scratch 602 towards each other and filled the distance between the scratch 602. The cell migration rate was about 91% after about 24 hours, which is an acceptable result that can be attributed to the presence of the Tragacanth, ZnO nanoparticles, and the Ammoniacum nanocapsules on the wound dressing which improves the wound healing process.

Referring to FIGS. 6A and 6C, the controlled release of the Ammoniacum extract from the polymeric matrix of the Tragacanth leads to higher cell migration rate on the second day. Therefore, the created scratch 602 was disappeared after about 48 hours and the cell migration rate reached 100%.

Example 6

Skin Sensitivity Assay of the Wound Dressing

The skin sensitivity and irritation of wound dressings can lead to clinical problems for patients. Therefore, evaluation of the skin sensitivity of the exemplary wound dressing is necessary. In this example, skin sensitivity of the wound dressing, which was prepared as described in exemplary embodiments of the present disclosure, was investigated through hypodermic injection of a solution containing different components of the exemplary wound dressing to rats.

The injected solution included Tragacanth, ZnO nanoparticles synthesized in presence of Tragacanth gum, and Ammoniacum nanocapsules. After the hypodermic injection, skin erythema and edema as the signs of skin sensitivity were studied before and about 72 hours after the injection. The result of this study shows that the injected solution does not induce any edema or erythema on the rat skin. Therefore, the composition of the wound dressing is safe and does not cause any local irritation or skin sensitivity.

Example 7

Release Behaviour of the Ammoniacum Extract From the Wound Dressing

In this example, the release behavior of the Ammoniacum extract from the Ammoniacum nanocapsules of the wound dressing was investigated. At first, an exemplary wound dressing, which was prepared as described in exemplary embodiments of the present disclosure, was immersed in an aqueous medium and stirred for different periods of time.

After stirring, ultraviolet-visible (UV-Vis) spectroscopy was used for the aqueous medium to measure the amount of the released Ammoniacum extract. TABLE. 2 represents results of the UV-Vis spectroscopy of the aqueous medium after immersing the wound dressing for different time periods at wavelengths of about 235 nm and about 295 nm.

TABLE 2

Results of the UV-Vis spectroscopy of the aqueous medium after immersing the wound dressing

| | Absorbance intensity | |
|---|---|---|
| Time (hour) | Wavelength of 235 nm | Wavelength of 295 nm |
| 2 | 0.51 | 0.39 |
| 4 | 0.70 | 0.58 |
| 6 | 0.89 | 0.79 |
| 8 | 1.05 | 0.97 |
| 12 | 1.18 | 1.10 |
| 18 | 1.32 | 1.24 |
| 24 | 1.45 | 1.36 |

Referring to TABLE. 2, after about twenty-four hours of immersing the exemplary wound dressing in the aqueous medium, the absorbance intensity of the aqueous medium increased from about 0.51 to about 1.45 at the wavelength of about 235 nm, and from about 0.39 to about 1.36 at the wavelength of about 295 nm. The results do not show any immediate release, and the Ammoniacum extract has a controlled and prolonged release from the Ammoniacum nanocapsules which were stabilized on the wound dressing. Therefore, the exemplary wound dressing has a high durability and does not need to be replaced for a long time.

Example 8

Swelling Behavior of the Wound Dressing

Water absorption is one of the most important properties of wound dressings that lead to create and maintain a moist environment on the wound site. Presence of the moist environment on the wound site provides a suitable condition for accelerating the wound healing process. In this example, swelling behavior of an exemplary wound dressing, which was prepared as described in the present disclosure, was investigated.

Three samples of the exemplary wound dressing were immersed in water for about twenty-four hours. After that swelling percentage was calculated for each sample. The swelling percentage is equal to the weight ratio of water in the swell sample to the dry sample. The results indicated that the swelling percentage of the exemplary wound dressing was about 86%. This high value of the swelling percentage of the exemplary wound dressing can be attributed to the hydrophilic property of hydroxyl and carboxyl groups in the Tragacanth of the wound dressing which creates hydrogen bond with water molecules.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in the light of the attached claims and their equivalents. Also, various modifications and changes may be made within the scope of the attached claims.

What is claimed is:

1. A method for preparing a wound dressing, comprising:
   forming a first solution by mixing a zinc solution with a first portion of a tragacanth solution;
   immersing a substrate in the first solution;
   forming a second solution by adjusting potential of hydrogen (pH) of the first solution containing the substrate;
   forming a modified substrate by synthesizing a plurality of zinc oxide (ZnO) nanoparticles with a particle size between 55 nm and 70 nm on the substrate by applying ultrasound radiation to the second solution; and
   forming a plurality of ammoniacum nanocapsules with a particle size between 20 nm and 80 nm utilizing the modified substrate, wherein forming the plurality of ammoniacum nanocapsules comprises:
      forming a first microemulsion by adding an emulsifier to a mixture of ammoniacum extract and an oil;
      forming a second microemulsion by adding a second portion of a tragacanth solution to the first microemulsion;
      immersing the modified substrate in the second microemulsion;
      adding a cross-linking agent to the second microemulsion containing the modified substrate; and
      applying ultrasound radiation to the second microemulsion containing the modified substrate and the cross-linking agent.

2. The method according to claim 1, wherein forming the first solution by mixing the zinc solution with the first portion of the tragacanth solution comprises mixing the zinc solution with a zinc (Zn) concentration between 0.05 M and 0.2 M and the first portion of the tragacanth solution with a tragacanth concentration between 0.5 and 1.5 weight percent.

3. The method according to claim 1, wherein the substrate comprises a cellulosic-based substrate.

4. The method according to claim 1, wherein forming the second solution by adjusting pH of the first solution containing the substrate comprises adding an alkaline solution dropwise to the first solution containing the substrate to adjust the pH between 7 and 8.

5. The method according to claim 1, wherein forming the modified substrate by synthesizing a plurality of ZnO nanoparticles on the substrate by applying ultrasound radiation to the second solution comprises applying the ultrasound radiation with a cycle between 0.4 and 1 with an amplitude between 30% and 100%.

6. The method according to claim 1, wherein the emulsifier comprises a hydrophilic-lipophilic balance (HLB) of more than 10.

7. The method according to claim 6, wherein forming the first microemulsion comprises adding a solution of the emulsifier with a concentration between 0.05 M and 0.2 M to the mixture of the ammoniacum extract and the oil.

8. The method according to claim 1, wherein the oil comprises one of almond oil, sesame oil, coconut oil, or combinations thereof.

9. The method according to claim 1, wherein the second portion of the tragacanth solution has tragacanth with a concentration between 0.5 and 1.5 weight percent.

10. The method according to claim 1, wherein the cross-linking agent comprises aluminum chloride, calcium chloride, or combinations thereof.

11. The method according to claim 1, wherein adding the cross-linking agent to the second microemulsion containing the modified substrate comprises adding a solution of the cross-linking agent with a concentration between 1.5 and 3 weight percent.

12. The method according to claim 1, wherein applying the ultrasound radiation to the second microemulsion containing the modified substrate comprises applying the ultrasound radiation with a cycle between 0.4 and 1 and an amplitude between 30% and 100%.

13. The method according to claim 1, wherein applying the ultrasound radiation to the second microemulsion containing the modified substrate comprises applying the ultrasound radiation for a time period between 4 minutes and 10 minutes.

* * * * *